United States Patent [19]

Chemburkar et al.

[11] Patent Number: 5,213,807
[45] Date of Patent: May 25, 1993

[54] PHARMACEUTICAL COMPOSITION CONTAINING IBUPROFEN AND A PROSTAGLANDIN

[76] Inventors: Pramod B. Chemburkar, 48 Long Ridge Rd., Randolph, N.J. 07869; Bahram Farhadieh, 965 Sunrise Rd., Libertyville, Ill. 60048; Barbara J. Struthers, 1706 Garand Dr., Deerfield, Ill. 60015; Tugrul T. Kararli, 8335 N. Kildare, Skokie, Ill. 60076; Steven C. Schumann, 10 N. 819 S. Airlite St., Elgin, Ill. 60123

[21] Appl. No.: 663,183

[22] Filed: Feb. 26, 1991

Related U.S. Application Data

[63] Continuation-in-part of Ser. No. 518,364, May 3, 1990, abandoned.

[51] Int. Cl.$^5$ ............................................. A61K 9/24
[52] U.S. Cl. .................................... 424/472; 514/530; 514/557; 514/570
[58] Field of Search ........................................ 424/472

[56] References Cited

U.S. PATENT DOCUMENTS

| | | | |
|---|---|---|---|
| 3,048,526 | 1/1962 | Boswell | 424/472 |
| 4,308,251 | 1/1981 | Dunn | 424/469 |
| 4,432,980 | 1/1984 | Fleming | 514/267 |
| 4,758,434 | 1/1988 | Kivonilus et al. | 424/949 |
| 4,844,907 | 1/1989 | Elger | 424/472 |
| 4,865,849 | 1/1989 | Conte et al. | 424/472 |
| 4,867,987 | 1/1989 | Slah | 424/480 |
| 4,873,231 | 1/1989 | Smith | 514/557 |
| 4,900,558 | 1/1990 | Barry et al. | 424/461 |
| 4,906,670 | 1/1990 | Higashi et al. | 514/993 |
| 4,944,949 | 1/1990 | Story et al. | 424/451 |

FOREIGN PATENT DOCUMENTS

| | | | |
|---|---|---|---|
| 165094 | 1/1950 | Austria | 424/472 |
| 1945511 | 1/1971 | Fed. Rep. of Germany | 424/472 |
| 1022171 | 1/1966 | United Kingdom | 424/472 |
| 1233055 | 1/1971 | United Kingdom | 424/472 |
| 1346610 | 1/1974 | United Kingdom | 424/472 |
| 2123289 | 1/1984 | United Kingdom | 424/472 |

OTHER PUBLICATIONS

James et al. Hyperalgesia after treatment of mice with etc. Arzneimittelforschung 28 804–7 Jan. 1978.
Mikami et al. The Potentiating effects of prostaglandins on etc. J. Pharm. Pharmacol. 31 856–7 Jan. 1979.
Walter et al. Effects of analgesics on bradykin-induced etc. Agents and Actions 27 375–7 Jan. 1979.
Taiwo et al. Prostaglandins Inhibit Endogenous Pain Control etc. J. Neurosci. 8 1346–9 Jan. 1988.
Pateromichelakis et. Prostaglandin E1-induced sensitization of Aa etc. Brain Research 232 89–96 Jan. 1982.
Sanyal et al. Prostaglandins: antinociceptive effect of etc. Clin. Exp. Pharmacol. Physiol. 4 247–55 Jan. 1977.
Bhattacharya et al. Potentiation of antinociceptive action of etc. Clin. Exp. Pharmacol. Physiol. 2 353–357 Jan. 1975.
Ferri et al. Decreased antinociceptive effect of morphine etc. Psychopharmacologia 39 231–5 Jan. 1974.
Sanyal et al. The antinociceptive effect of etc. Psychopharmacology 60 159–63 Jan. 1979.
G. D. Searle & Co. CYTOTEC (misoprostol) Drug Information Physician's Desk Reference 44 2056–7 Jan. 1990.
IMS IMS Marketletter IMS Marketletter Jun. 1987.

*Primary Examiner*—Shep K. Rose

[57] ABSTRACT

A pharmaceutical composition includes a core of an NSAID selected from ibuprofen and ibuprofen salts, which core is surrounded by an intermediate coating impermeable to the passage of ibuprofen and a mantle coating which includes a prostaglandin surrounding the coated ibuprofen core.

14 Claims, 1 Drawing Sheet

PHARMACEUTICAL COMPOSITION CONTAINING IBUPROFEN AND A PROSTAGLANDIN

This is a continuation-in-part, of application Ser. No. 07/518,364, filed May 3, 1990 now abandoned.

BACKGROUND OF THE INVENTION

The invention herein is directed to a new pharmaceutical composition which consists of a generally trilayer tablet having an inner core, an intermediate barrier coating and an outer mantle coating surrounding the inner core. The inner core includes the NSAID ibuprofen or a salt of ibuprofen. The mantle coating includes a prostaglandin, described hereinafter in more detail.

Nonsteroidal anti-inflammatory drugs (NSAIDs) comprise a class of drugs which have long been recognized as having high therapeutic value especially for the treatment of inflammatory conditions such as exhibited in inflammatory diseases like osteoarthritis (OA) and rheumatoid arthritis (RA). While the NSAIDs present a beneficial therapeutic value they also exhibit undesirable side effects. An especially undesirable side effect of the administration of NSAIDs is the ulcerogenic effects generally associated with chronic use. The chronic use of NSAIDs, the use of high dosages of NSAIDs and the use of NSAIDs by the elderly can lead to NSAID induced ulcers. NSAID induced ulcers in the stomach can be dangerous. Such ulcers generally exhibit little or few symptoms and may cause dangerous bleeding when undetected. In some instances, bleeding ulcers can prove fatal. The U.S. Food and Drug Administration requires a class warning for all NSAIDs, which states: Serious gastrointestinal toxicity such as bleeding, ulceration, and perforation can occur at any time, with or without warning symptoms, in patients treated chronically with NSAID therapy.

Certain prostaglandins have been shown to prevent NSAID induced ulcers. Acceptable prostaglandin compounds for the invention herein and their preparation are described in U.S. Pat. Nos. 3,965,143, 4,060,691, 4,271,314, and 4,683,328. The prostaglandin compound commercially available under the USAN (United States Adopted Name) name misoprostol is a pharmaceutically acceptable prostaglandin which has been accepted for use in the treatment of NSAID induced ulcers in many countries, including the United States. Misoprostol is commercially available as a stabilized formulation by prescription in such countries. The stabilized formulation is described in U.S. Pat. No. 4,301,146.

While prostaglandins are beneficial compounds and have found therapeutic usage, prostaglandins are generally considered highly unstable. Therefore, it is desirable to find prostaglandins with the desired anti-ulcerogenic properties and which can be stabilized or provided in stabilized formulations especially with respect to contemplated oral methods of delivery.

It would be desirable to provide a pharmaceutical composition which would exhibit the beneficial properties of an NSAID and which composition would exhibit the beneficial properties of a prostaglandin for countering (by inhibiting, reducing or preventing) the ulcerogenic side effects attendant to NSAID administration.

SUMMARY OF THE INVENTION

The invention herein is directed to a pharmaceutical composition comprising a core consisting of an NSAID selected from ibuprofen and ibuprofen salts. An intermediate barrier coating surrounds the core. Such an intermediate coating prevents contact between the NSAID and the prostaglandin to thereby inhibit any deleterious or otherwise non-beneficial interaction of the NSAID and prostaglandin such as degradation of the prostaglandin by the NSAID. A mantle coating of a prostaglandin surrounds the core and intermediate coating. The prostaglandin preferably is an orally available prostaglandin. Acceptable prostaglandins for use herein include prostaglandins having the following structure

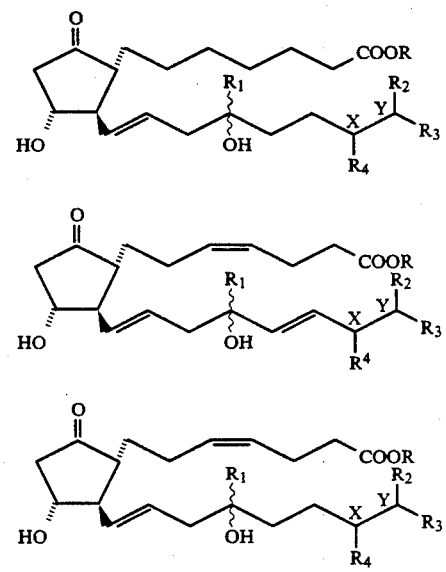

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ or $R_4$ together with carbons X and Y form a cycloalkenyl having 4 to 6 carbon atoms and wherein the X-Y bond can be saturated or unsaturated.

An especially preferred pharmaceutical composition herein has a structure wherein the core comprises the NSAID ibuprofen in a therapeutic amount such as from 300 to 800 milligrams (mg), an intermediate coating comprising a material substantially impervious/impermeable to the passage of ibuprofen, and a mantle coating surrounding the core comprising the prostaglandin misoprostol in a therapeutic amount of 100 to 200 micrograms (mcg). An especially preferred intermediate coating can be formed from a crystalline-forming material such as a sugar, and more specifically sucrose.

The invention herein will be more fully understood with regard to the following brief description of the accompanying drawings and the following detailed description.

DETAILED DESCRIPTION OF THE DRAWINGS

Figure 1:
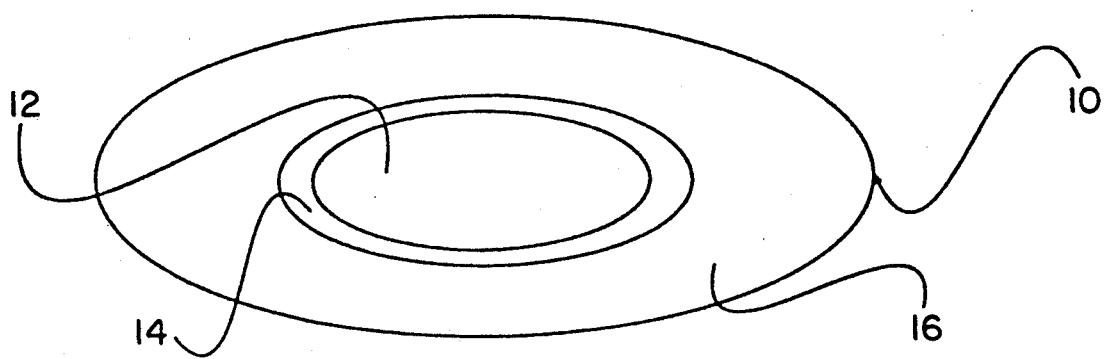
FIG. 1 is a schematic representation of a tablet comprising the pharmaceutical composition herein.

The invention herein is directed to a pharmaceutical composition which is a generally an oral trilayer tablet. The tablet has a core comprising the nonsteroidal anti-inflammatory drug (NSAID), ibuprofen and ibuprofen salts. Ibuprofen is the USAN name for (±)-2-(p-isobutylphenyl)-propionic acid. Surrounding the core is an intermediate coating comprising a substantially impervious/impermeable material to the passage of ibuprofen. An especially preferred intermediate coating can be formed from a crystalline forming material such as a sugar, and more specifically sucrose. Surrounding the core and intermediate coating is a mantle coating which comprises a prostaglandin of the structure

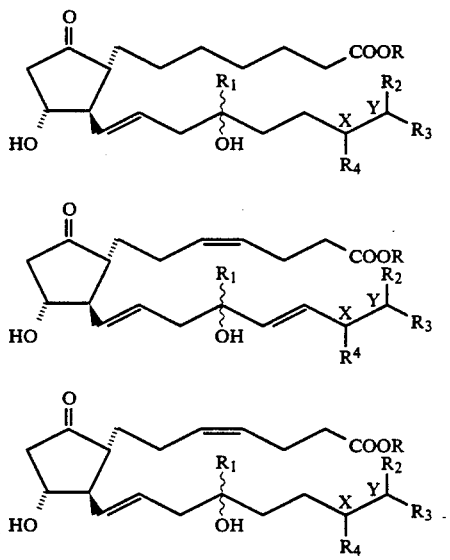

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ or $R_4$ together with carbons X and Y form a cycloalkenyl having 4 to 6 carbon atoms and wherein the X-Y bond can be saturated or unsaturated.

The pharmaceutical composition herein can be described with regard to the accompanying drawings wherein FIG. 1 schematically represents the preferred embodiment of the composition herein.

FIG. 1 represents a cross sectional view of a pharmaceutical composition herein. The pharmaceutical composition consists of a generally trilayer tablet 10 which can have any geometric shape but, as is shown in FIG. 1, is preferably a bi-convex tablet. It should be noted that a bi-convex tablet can have a cylindrical shape between the convex surfaces, although for ease of description herein an oval cross section is shown. The tablet 10 includes an inner core 12 which includes as a pharmaceutically active component the NSAID consisting of ibuprofen or its salt. The inner core 12 can be formulated by compressing the ibuprofen or ibuprofen salts in any suitable tableting equipment. Standard compression tableting techniques can be employed for forming the core.

The ibuprofen can be present in any therapeutically acceptable amount. For normal dosing of ibuprofen, ibuprofen is administered in a dosing range from 400 mg to 3200 mg per day. The Physicians' Desk Reference, 44th Edition, states that the recommended dosage for osteoarthritis and rheumatoid arthritis is 1200 to 3200 mg per day in divided doses. For mild to moderate pain the recommended dosage is 400 mg every 4 to 6 hours as necessary for relief of pain. For dysmenorrhea the recommended dosage is 400 mg every 4 hours as necessary for the relief of pain. The inner core for the pharmaceutical composition herein therefore can be in an amount to accomplish such a dosing regimen and can contain from 150 to 800 mg of ibuprofen and preferably in a dosage of 400 mg. Various pharmaceutically acceptable excipients can be combined with the ibuprofen or ibuprofen salt as is well known in the pharmaceutical art, including the inactive ingredients listed in the PDR 44th edition for ibuprofen as sold under the brand name and trademark MOTRIN by The Upjohn Company.

If the inner core is an ibuprofen salt, the ibuprofen salt can be present in a therapeutically acceptable amount as is referred to in the above discussion with respect to the acid.

Surrounding the core 12 is a barrier coating or an intermediate coating 14. The intermediate barrier coating 14 can be any suitable coating which prevents passage of the ibuprofen. Ibuprofen is a compound that exhibits sublimation. Therefore an intermediate coating material is selected from those materials which prevent the passage of ibuprofen in such a vapor phase and are, therefore, substantially impervious to the passage of ibuprofen. The term "substantially impervious to the passage of ibuprofen" used herein describes the intermediate barrier coating and means that the coating is formed from a material that when coated onto the core substantially prevents the migration of ibuprofen from the core through the intermediate coating. It was found herein that an intermediate barrier coating could be formed using crystalline forming materials. An especially preferred crystalline forming material is sucrose. The intermediate coating can have sufficient crystallinity for preventing the passage (diffusion) of ibuprofen through the intermediate coating. Sufficient crystallinity is used herein to mean either a crystalline or partially crystalline state. Partially crystalline includes a mixture of crystalline and amorphous states of the material. Other pharmaceutically acceptable excipients commonly used in sugar coating processes such as fillers (calcium carbonate, talc, titanium dioxide), colorants (dyes, aluminum lakes, iron oxides, titanium dioxide), film formers (acacia, gelatin, cellulose derivatives, starch), antiadhesives (talc), flavors, surfactants and dusting powders (colloidal silicone dioxide, calcium sulfate, starch), and the like can be present in the intermediate coating but which do not inhibit the ability of the intermediate coating to prevent the diffusion of ibuprofen therethrough.

An especially preferred class of compounds which can be used include crystalline forming sugars and more preferably sucrose. Sucrose is especially preferred as it exhibits sufficient crystalline properties (including up to 55° C.) and it remains in the crystalline state and does not absorb any appreciable amounts of water up to a very high relative humidity value (84%).

Standard tablet coating techniques can be employed to coat the intermediate coating on the core of the tablet. Acceptable sugar coating techniques are disclosed in *Pharmaceutical Dosage Forms: Tablets*, Volume 3, Second Edition, Revised and Expanded, by Lieberman, Lachman and Schwartz,(1990) at pages 78-93, "Sugar Coating," by Porter and Bruno.

The intermediate coating 14 segregates the NSAID from the prostaglandin. The intermediate coating 14 prevents the degradation of the prostaglandin by the presence of the NSAID as the intermediate coating maintains the two active components separate. Studies have shown that an admixture of misoprostol and ibuprofen is undesirably unstable for a commercially acceptable product. Solid state stability studies have shown that misoprostol is extremely unstable in the presence of ibuprofen and degrades at a rapid rate. A 10:1 mixture of ibuprofen:misoprostol stored at 55° C. yields only 44% misoprostol after 4 days and only 18% after storage at 65° C. for 3 days. It is, therefore, highly desirable to formulate a composition (dosage form) which would effectively separate the two active ingredients while providing a delivery system for each ingredient. Additional studies have shown that an intermediate coating of certain polymers is unacceptable due to ibuprofen bleed through of the polymer which ibuprofen then interacts with and degrades the misoprostol. It is desirable to have an intermediate coating which substantially prevents the diffusion of ibuprofen as the amount of ibuprofen present in the tablet is between 150-800 mg and the amount of prostaglandin is about 50-500 μg. A small amount of ibuprofen diffused through the intermediate coating can be undesirable as it can degrade and lessen the therapeutically available amount of prostaglandin.

The intermediate coating can be coated onto the inner core using standard coating techniques. For example, aqueous or solvent coating techniques can be used to apply the coating to the inner core.

The mantle coating 16 surrounds the inner core of the NSAID and the intermediate coating, encapsulating the intermediate coated NSAID core. The mantle coating includes a prostaglandin and more preferably an orally available prostaglandin. The mantle coating can be applied by compression coating or solvent coating techniques such as are well known in the tableting art.

The terms "prostaglandin" and/or its accepted acronym "PG" or, as more appropriately for the E-series prostaglandins, "PGE," are used herein to refer to naturally occurring or man-made E-series prostaglandins and their analogs and derivatives.

It has been found herein that acceptable prostaglandins include the E₁ prostaglandins shown by the following Formula I

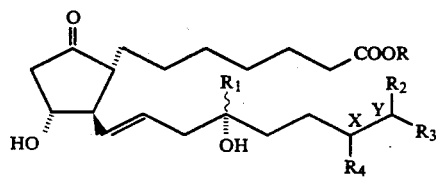

E₂ prostaglandins shown by the following Formula II

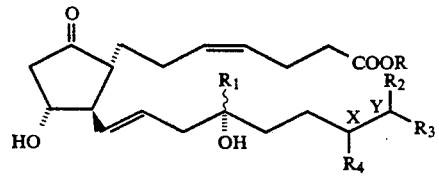

and E₃ prostaglandins shown by the Formula III

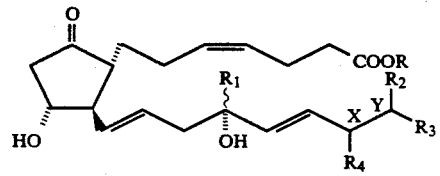

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cloalkenyl having 4 to 6 carbon atoms or $R_3$ or $R_4$ together with carbons X and Y form a cycloalkenyl having 4 to 6 carbon atoms and wherein the X-Y bond can be saturated or unsaturated.

By lower alkyl is meant straight or branched chain alkyl such as methyl, ethyl, propyl, isopropyl, butyl, secondary butyl or tertiary butyl, pentyl, or hexyl with the indicated limitation of the number of carbon atoms.

With regard to the illustrated structures, the dashed line indicates the grouping being behind the plane of the paper and the solid, blackened triangular shape indicates that the group is in front of the plane of the paper.

It has been found herein that acceptable prostaglandins include the prostaglandin misoprostol (commercially available as CYTOTEC® by G. D. Searle & Co.) represented by the following Formula:

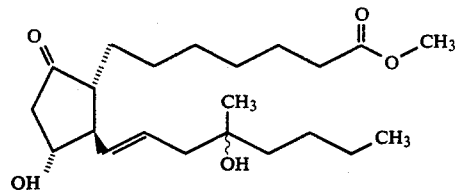

the prostaglandin enisoprost, (±)methyl 11a, 16-dihydroxy-16-methyl-9-oxoprosta-4Z,13E-dien-1-oate represented by the following Formula:

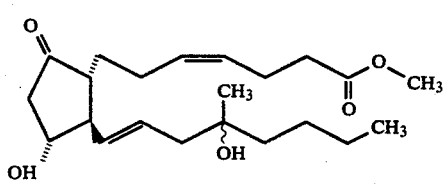

and the prostaglandin methyl 7-[2B-[6-(1-cyclopenten-1-yl)-4-hydroxy-4-methyl-1E,5E-hexadienyl]-3a-hydroxy-5-oxo-1R,1a-cyclopentyl]-4Z-heptenoate represented by the following formula:

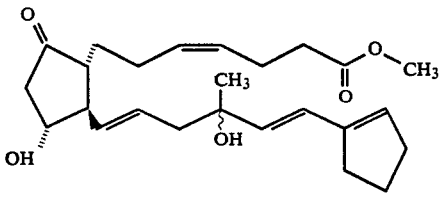

With regard to the illustrated structures, the dashed line indicates the grouping being behind the plane of the paper and the solid, blackened triangular shape indicates that the group is in front of the plane of the paper.

The prostaglandins useful in the composition herein can be prepared by known reaction schemes such as by the methods taught in U.S. Pat. Nos. 3,965,143, 4,271,314 and 4,683,328. The individual isomers can be obtained by chromatographic separation.

When the prostaglandin is misoprostol, (±)methyl 11a,16-dihydroxy-16-methyl-9-oxoprost-13E-en-1-oate, the misoprostol can be present in an amount from 50 to about 500 mcg and preferably from 100 to about 200 mcg. The mantle coating can also contain pharmaceutically acceptable excipients. For example, the excipients listed in the PDR for CYTOTEC brand of misoprostol can be included.

The invention will be further understood with regard to the following examples. In the Examples 1-3 the misoprostol was coated on the sugar coated ibuprofen core in the following manner.

Coating of Sugar Coated Cores with Misoprostol

The procedures were similar to those described in Example 4 hereinafter. The tablet charge was approximately 480 gm (500 tablets).

a) Aqueous coating: 400mg following sequence
1st coat-2% aqueous HPMC (with & without propylene glycol as a plasticizer)
2nd coat-Misoprostol/HPMC dispersion in isopropyl alcohol:water (1:4)
3rd coat-2% aqueous HPMC (with & without propylene glycol)

b) Hydroalcoholic Misoprostol Coating: A solvent coating method for the application of misoprostol to sugar coated tablets used the following coating solution:

| Ingredient | % w/w |
| --- | --- |
| Misoprostol:HPMC Dispersion | 1.17 |
| HPMC (6 cps) | 4.50 |
| Isopropyl Alcohol 99% | 85.78 |
| Water | 8.53 |

To prepare above solution, the misoprostol dispersion was dispersed in the alcohol and mixed well. The HPMC was then added and mixed until uniform. Finally, the water was added and the solution was mixed until ready to use. The 400 mg tablets were coated with 50 mcg of misoprostol in a 2.1% layer of HPMC.

EXAMPLE 1

A pharmaceutical composition was prepared consisting of an ibuprofen central core, a sucrose intermediate coating and a misoprostol mantle. The tablet had the following composition.

| Component | Unit Fomula (mg) |
| --- | --- |
| Ibuprofen Core | |
| ibuprofen | 400.00 |
| pregelatinized cornstarch | 155.00 |
| croscarmallose sodium | 43.00 |
| stearic acid | 12.30 |
| Intermediate Coating | |
| sugar (sucrose) | 29.00 |
| acacia | 5.00 |
| colloidal silicon dioxide | 4.60 |
| calcium sulfate | 77.00 |
| starch U.S.P. | 41.0 |
| Mantle Coating | |
| misoprostol:HPMC dispersion (1:100) | |
| misoprostol | 0.10 |
| hydroxypropyl methylcellulose | 9.90 |
| HPMC 6 cps (Pharmacoat 606) | 58.50 |

EXAMPLE 2

A pharmaceutical composition was prepared consisting of an ibuprofen central core, a sucrose intermediate coating and a misoprostol mantle. The tablet had the following composition.

| Component | Unit Formula (mg) |
| --- | --- |
| Ibuprofen Core | |
| ibuprofen | 600.00 |
| pregelatinized cornstarch | 155.00 |
| croscarmallose sodium | 43.00 |
| stearic acid | 12.30 |
| Intermediate Coating | |
| sugar (sucrose) | 29.00 |
| acacia | 5.00 |
| colloidal silicon dioxide | 4.60 |
| calcium sulfate | 77.00 |
| starch U.S.P. | 41.00 |
| Mantle Coating | |
| misoprostol:HPMC dispersion (1:100) | |
| misoprostol | 0.20 |
| hydroxy propyl methyl cellulose | 20.0 |
| HPMC 6 cps (Pharmacoat 606) | 58.50 |

EXAMPLE 3

A pharmaceutical composition was prepared consisting of an ibuprofen central core, a sucrose intermediate coating and a misoprostol mantle. The tablet had the following composition.

| Component | Unit Formula (mg) |
| --- | --- |
| Iburofen Core | |
| ibuprofen | 800.00 |
| pregelatinized cornstarch | 155.00 |
| croscarmallose sodium | 43.00 |
| stearic acid | 12.30 |
| Intermediate Coating | |
| sugar (sucrose) | 29.00 |
| acacia | 5.00 |
| colloidal silicon dioxide | 4.60 |
| calcium sulfate | 77.00 |
| starch U.S.P. | 41.00 |
| Mantle Coating | |
| misoprostol:HPMC dispersion (1:100) | |
| misoprostol | 0.20 |
| hydroxy propyl methyl cellulose | 20.0 |
| HPMC 6 cps (Pharmacoat 606) | 58.50 |

EXAMPLE 4

The polymers indicated in this Example 4 were applied as a seal coat at a 5% level based on weight gain. Some tablets were subsequently coated with misoprostol:HPMC dispersion. The coating trials were performed in a Freund Hi-Coater, Model HCT-30, using a Masterflex Peristaltic Pump for dosing. The following coating parameters were used for the coating experiments.

| | |
|---|---|
| Tablet Charge: | 600 gm (975 tablets) |
| Inlet Temperature: | 60° C. for aqueous formulations |
| | 40° C. for solvent formulations |
| Outlet Temperature: | 35–40° C. aqueous |
| | 29–30° C. solvent |
| Pan speed: | 15 rpm |
| Spray Rate: | 6 gm/min aqueous |
| | 5 gm/min solvent |
| Atomizing air: | 0.75 bar |

The following polymers were evaluated as barriers to ibuprofen sublimation. The determination of their abilities to perform as a barriers was made by bromocresol green (BCG) indicator or by misoprostol degradation. The BCG was applied in the outer coating of a tablet having an inner core of ibuprofen and the indicated intermediate coating. The BCG coating initially was a bright shade of blue when applied but as it came into contact with the acidic ibuprofen a color change occurred and shades of green to yellow were observed. A color change indicated that ibuprofen had penetrated the barrier coating. The following polymers were evaluated and a color change was noted, indicating that the polymer did not provide an adequate barrier to the passage of ibuprofen sufficient to prevent degradation of a prostaglandin sensitive to ibuprofen:
- Hydroxypropyl methylcellulose 6 cps (aqueous)
- Ethyl cellulose (aqueous)
- Eudragit E30D (aqueous)
- Eudragit E100 (ethanol)
- Polyvinyl alcohol (ethanol)
- Shellac (aqueous, ethanol)
- Polyvinyl acetate phthalate (aqueous)
- Cellulose acetate phthalate (methylene chloride-acetone)

EXAMPLE 5

The procedures of Example 4 were repeated and the following chemical barriers were evaluated to determine their efficacy as barriers to the passage of ibuprofen as the acid molecule.
Aluminum hydroxide/HPMC
Aluminum hydroxide/Eudragit E30D
Tricalcium Phosphate/HPMC
Calcium oxide/HPMC
Magnesium hydroxide/HPMC
Magnesium oxide/HPMC The observed stability data showed that rapid and extensive prostaglandin degradation would occur by ibuprofen passage for all of the chemical barriers tested. These chemical barriers being basic in nature were initially believed to be useful as barriers to the passage of the acidic ibuprofen. However, upon experimentation it was found that using the criteria of a base/acid analysis was insufficient in itself for selecting a barrier coating.

The composition that is the invention herein provides an ease of delivery of the NSAID ibuprofen for its therapeutic value such as the alleviation of inflammation in a system which limits the undesirable side effects of such NSAID therapy. That is, the composition herein consisting of a generally trilayer tablet provides a prostaglandin in combination with the NSAID ibuprofen whereby the prostaglandin can be administered for its beneficial therapeutic value in preventing and or inhibiting the incidence of NSAID induced ulcers.

A particularly beneficial aspect of the invention herein is that the combination of the two components in a trilayer tablet assures compliance with the therapeutic regimen of the two active components. That is, a co-administration of the active components (ibuprofen and prostaglandin) separately can be difficult to achieve and can be difficult for a patient to faithfully follow. By placing the two active components in the same tablet or composition, adherence to the therapeutic regimen is controlled as the administration of the tablet containing the NSAID assures compliance of the administration of the prostaglandin. Further, the selection of the configuration for the tablet with the NSAID in the core and the prostaglandin in the mantle coating provides a benefit, in that the prostaglandin can be first dissolved to provide its therapeutic benefit in the stomach, leaving the NSAID to be dissolved subsequently (whether in the stomach or due to the mantle and intermediate coating as well as the passage of time in the intestine) to provide its therapeutic benefit.

The composition herein is especially utile as the composition herein exhibits a stability for the prostaglandin and the ibuprofen in such a fixed combination as herein described.

We claim:

1. A pharmaceutical oral layered tablet composition comprising:
   a. a core comprising an NSAID selected from ibuprofen and ibuprofen salts;
   b. an intermediate barrier coating substantially impervious to the passage of ibuprofen, said barrier coating surrounding the core and being free of prostaglandin degrading polymers and chemicals; and
   c. a mantle coating surrounding the core and intermediate coating, comprising a prostaglandin unstable in the presence of ibuprofen and selected from a prostaglandin of the structural formula

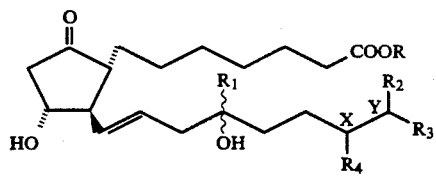

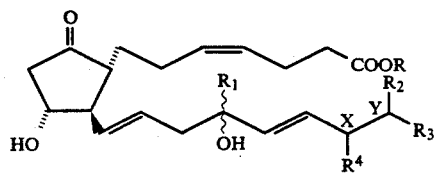

-continued

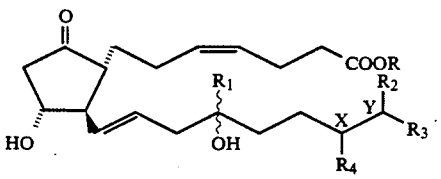

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl 1 to 4 carbon atoms or $R_2$ and $R_3$ together with carbon Y form a cycloalkenyl having 4 to 6 carbon atoms or $R_3$ or $R_4$ together with carbons X and Y form a cycloalkenyl having 4 to 6 carbon atoms and wherein the X-Y bond can be saturated or unsaturated.

2. A pharmaceutical composition as recited in claim 1 wherein the prostaglandin comprises a prostaglandin of the structural formula

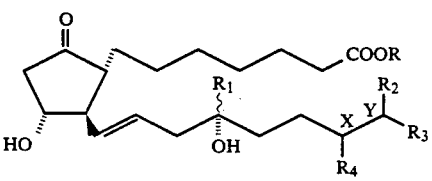

3. A pharmaceutical composition as recited in claim 2 wherein the prostaglandin comprises misoprostol.

4. A pharmaceutical composition as recited in claim 1 wherein the prostaglandin comprises the structural formula

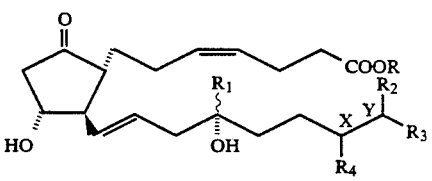

5. A pharmaceutical composition as recited in claim 4 wherein the prostaglandin comprises enisoprost.

6. A pharmaceutical composition as recited in claim 1 wherein the prostaglandin comprises a structural formula

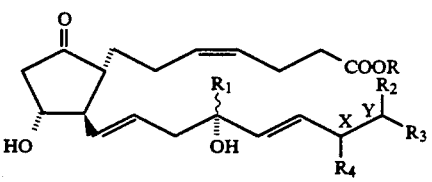

7. A pharmaceutical composition as recited in claim 1 wherein the NSAID comprises ibuprofen.

8. A pharmaceutical composition as recited in claim 1 wherein the NSAID comprises an ibuprofen salt.

9. A pharmaceutical composition as recited in claim 1 wherein the intermediate coating comprises a sucrose coating.

10. A pharmaceutical composition as recited in claim 1 wherein the prostaglandin mantle coating comprises a stabilized prostaglandin formulation.

11. A pharmaceutical composition as recited in claim 1 wherein the NSAID comprises ibuprofen in an amount from about 150 to 800 mg, the intermediate coating comprises sucrose and the mantle coating comprises a stabilized prostaglandin formulation containing about 100 to 200 mcg of misoprostol.

12. A pharmaceutical oral layered tablet composition comprising:
   a. a core comprising an NSAID selected from ibuprofen and ibuprofen salts;
   b. an intermediate barrier coating impervious to the passage of ibuprofen, said barrier coating surrounding the core, comprising a crystalline forming material and being free of prostaglandin degrading polymers and chemicals; and
   c. a mantle coating surrounding the core and intermediate coating, comprising a prostaglandin unstable in the presence of ibuprofen and selected from a prostaglandin of the structural formula

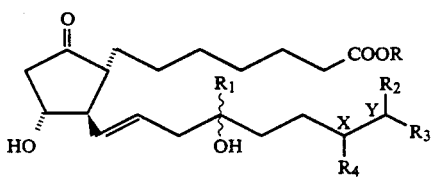

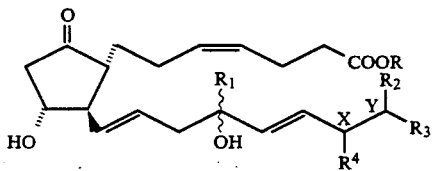

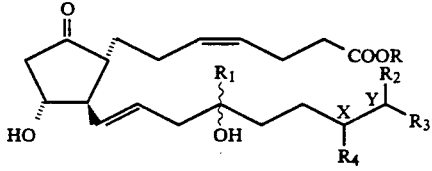

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ or $R_4$ together with carbons X and Y form a cycloalkenyl having 4 to 6 carbon atoms and wherein the X-Y bond can be saturated or unsaturated.

13. A pharmaceutical composition as recited in claim 12 wherein the intermediate coating comprises a sucrose coating.

14. A method of treating inflammation comprising administering to a patient in need of such treatment, a therapeutically effective amount of a composition according to claim 1.

* * * * *

UNITED STATES PATENT AND TRADEMARK OFFICE
CERTIFICATE OF CORRECTION

PATENT NO. : 5,213,807
DATED : May 25, 1993
INVENTOR(S) : Chemburkar, et al.

It is certified that error appears in the above-identified patent and that said Letters Patent is hereby corrected as shown below:

```
Column 6, line 10, reading "by the Formula" should read -- by
the following Formula --.

Column 6, line 25, reading "form a cloalkenyl" should read --
form a cycloalkenyl --.

Column 11, line 15, reading "alkyl 1 to 4" should read --
alkyl having 1 to 4 --.
```

Signed and Sealed this

Tenth Day of January, 1995

*Attest:*

BRUCE LEHMAN

*Attesting Officer*     *Commissioner of Patents and Trademarks*